United States Patent [19]

Scholefield

[11] 4,094,745

[45] June 13, 1978

[54] METHOD OF STAINING MICROSCOPIC ORGANISMS

[76] Inventor: John Scholefield, Glenesk, Moor Road, Milngavie, Glasgow, Scotland

[21] Appl. No.: 701,083

[22] Filed: Jun. 30, 1976

Related U.S. Application Data

[63] Continuation-in-part of Ser. No. 479,583, Jun. 14, 1974, abandoned.

[30] Foreign Application Priority Data

Jun. 22, 1973  United Kingdom .............. 29674/73

[51] Int. Cl.² ............................................. C12K 1/04
[52] U.S. Cl. .................................. 195/103.5 M; 424/7
[58] Field of Search ................ 195/103.5 M; 8/31, 72; 424/3, 7

[56] References Cited

U.S. PATENT DOCUMENTS

| | | | |
|---|---|---|---|
| 3,670,072 | 6/1972 | Mauthner ................................. | 424/3 |
| 3,678,151 | 7/1972 | Horonick et al. ...................... | 424/3 |
| 3,790,447 | 2/1974 | Hirata et al. .................. | 195/103.5 R |

FOREIGN PATENT DOCUMENTS 275,314  10/1970  U.S.S.R.

OTHER PUBLICATIONS

Lamanna, et al., Basic Bacteriology, The Williams and Wilkins Co., Baltimore, Md., 1965, 3rd ed. (pp. 108–110, 125–127, 134, 136, 137, 146, 147, 151, 152 & 154–159).

*Primary Examiner*—David M. Naff
*Attorney, Agent, or Firm*—Mason, Fenwick & Lawrence

[57] ABSTRACT

A rapid method of staining microorganisms with fluorochrome dyes to render them readily visible when illuminated with U.V. radiation and viewed under a microscope is described. The method involves chemical treatment of a sample containing microorganisms suspended in a liquid medium with phosphate ions to modify (chemically) the dye-receptor sites in the microorganisms and then staining the treated microorganisms with a fluorochrome dye. Suitable additional treatments which enhance fluorescence are also possible, including methylation, esterification, hydrolysis, oxidation and treatment with sulphur dioxide. The method is particularly advantageous in the microscopic enumeration of microorganisms. Also certain techniques are described which permit the determination of viable and non-viable cells.

10 Claims, No Drawings

METHOD OF STAINING MICROSCOPIC ORGANISMS

The present invention is a continuation-in-part of my application U.S. Ser. No. 479,583 filed June 14, 1974 and now abandoned.

This invention relates to a method of staining microorganisms. In particular, the present invention relates to a procedure for estimating the extent of microbial contamination in foodstuffs or raw materials used in the production of foodstuffs. However, the field of application of the invention is not limited to food science; it may be used in any situation where the estimation of microorganisms is required, for example, in fermentation industries, yeast manufacture, in medical diagnosis and in the manufacture of pharmaceutical products.

The conventional procedure employed in determining the number of microorganisms in a material involves isolation of the microorganisms from the material and cultivation of the isolated microorganisms on a culture medium on a plate. The enumeration of the microorganisms by this 'colony count' technique is a lengthy procedure which, under normal circumstances, would take about two days for incubation, depending on the nature and number of the microorganisms involved, but it is not uncommon for the incubation to take a week or more. When incubation is complete, the number of colonies of microorganisms on the plates is determined visually. This 'colony-count' technique is inherently inaccurate, the errors arising because not all the microorganisms may be recovered from the material under examination. Some are killed during preparation of the sample before application to the culture medium; also culturing conditions during incubation may not be appropriate for all types of microorganisms in the sample. Thus some of the types may not form colonies and will, therefore, not be estimated by the technique. Additionally, it is known that a single colony may arise from the growth of more than one microorganism.

By far the most significant disadvantage of the colony-count technique is the length of time required to obtain a result. Often, with a foodstuff, by the time a report has been issued, the material held in storage awaiting the report has deteriorated in quality. It will be appreciated that it is highly uneconomic to store large quantities of food materials, often in expensive refrigerated warehouse space, over lengthy periods of time awaiting a laboratory report on its microbial contamination. It is even more uneconomic when the material ultimately fails to satisfy prescribed standards.

Another disadvantage of conventional colony-count methods of enumerating microorganisms is that only viable cells are counted.

Another technique commonly used in food technology is to stain a glass slide preparation of the foodstuff with a dye, such as methylene blue, and then to examine the stained smear microscopically. The disadvantage of this method is that the food itself becomes stained, forming a coloured background against which the microorganisms are difficult to detect. The method has some value as a coarse measurement of contamination in samples of high levels of mircobial contamination. At low levels of contamination, the test is inaccurate.

In diagnostic medicine a qualitative technique known as the "fluorescent-antibody technique" (F.A.T.) is used. In this technique, a fluorochrome dye is chemically combined with antiserum of a specific group of microorganisms. The fluorochrome-labelled antiserum is mixed with an extract from the material under test and, if the specific group of micro-organisms is present, a reaction takes place which results in making the specific group of microorganisms fluoresce on illumination. While this technique is useful for the identification of specific groups of microorganisms, it is too specific for quantifying the general microbial content of a material.

An object of the present invention is to provide a method of staining microorganisms with a fluorochrome dye to obtain enhanced fluorescence under U.V. illumination.

According to the present invention there is provided a method of staining microorganisms comprising treating the microorganisms with an aqueous solution of a phosphate and reacting the treated microorganisms with a fluorochrome dye, whereby said dye combines with the microorganisms via intermediate phosphate linkages.

The staining may be enhanced by additional treatment of the microorganisms by any one or more of the following chemical treatments selected from methylation, esterification, hydrolysis, oxidation, and treatment with sulphur dioxide.

Methylation may be effected by treating the sample on a carrier plate with an ethereal solution of diazomethane. Esterification may be effected with a sulphuric acid ester, preferably with control of time, temperature and pH.

Hydrolysis may be effected by treatment of the sample on a carrier plate with an acid selected from hydrochloric, perchloric, periodic, sulphuric or nitric. Oxidation may be effected with an oxidising agent. Preferably the time, temperature and pH of the treatment are controlled.

The treatment with sulphur dioxide may simply involve exposure of the sample on the carrier plate to a solution of sulphur dioxide or a salt thereof capable of releasing sulphur dioxide or a solution of thionyl chloride. Time, temperature and pH of the treatment are preferably controlled.

The method of the invention may be used to produce wet specimens or, alternatively, dry, fixed specimens on a carrier plate. The wet technique has the advantage of rapidity, whereas the advantage of the dry technique is that the sample may be subjected to a multiplicity of treatment steps without large volumes of reagent solutions accumulating. In the fixed sample preparations, between each treatment step the sample on the plate may be washed in water or a buffer solution preferably under controlled conditions of time, temperature and pH.

The dry preparation may be produced by applying a liquid sample of the phosphate derivatives of the microorganisms to a carrier plate, such as a microscope slide, a plastic film or an opaque plate or strip. For enumeration of microorganisms, a known volume of sample is applied to a known area of the carrier plate. After application of the sample to the plate the liquid is allowed to evaporate at ambient or elevated temperature. In practice, a unit volume of a liquid sample is applied to a carrier plate and the liquid allowed to evaporate either naturally or by application of heat. The cells of the microorganisms may then be fixed on the slide by heating same or by immersion in a solvent, such as alcohol, acetone, acetone-alcohol solution, alcohol-acetic acid solution and formaldehyde, followed by drying of the fixed preparation.

The fluorochrome dye may be selected from the group consisting of lissamine-rhodamine B, acridine orange, acridine yellow, primuline, ethidium bromide, acriflavine, eosin Y, auramine, tetramethyl-oxamethine-cyanine ester, rhodamine B, rhodamine 3G, fluorescein, fluorescein diacetate and thionin. The staining may be carried out simply by adding a solution of the fluorochrome dye or dyes to a suspension of the phosphate derivatives or by immersing the plate carrying a fixed sample in a solution or solutions of a dye or dyes, removing the plate, washing off excess dye or dyes and drying the plate in air or by the application of heat. The staining may be carried out under controlled time, temperature, pH and light conditions.

It is possible to use, in the performance of this invention, traditional staining techniques, such as counter-staining, to mask background interference. Also, it is sometimes advantageous to incorporate a treatment with an optical brightener to intensify fluoresence of the dye.

The stained preparation is examined under a microscope to enumerate or study the microorganisms therein.

While not wishing to be bound by any particular theory, it is believed that the staining technique of this invention involves, at a basic level, reaction of the dye with D.N.A. molecules in the cells of the microorganisms. When a microorganism is exposed to a dye, one molecule of dye links to the microorganism at each of certain locations in the D.N.A. molecule (dye-receptor sites). Treatment with phosphate ion forms, at each dye-receptor site, a phosphate bridge to which more than one molecule of dye may then link. Thus the uptake of dye by the microorganism is increased, resulting in increased fluorescence from each microorganism when viewed under U.V. light.

Each of the additional treatments mentioned above, i.e. methylation, esterification, hydrolysis, oxidation and treatment with sulphur dioxide, it is believed, modify the D.N.A. molecule to form additional dye-receptor sites. It is thought that the formation of additional aldehyde and carboxylic acid groups contributes to the reaction mechanism.

The invention also permits discrimination between viable and non-viable microorganisms, and it may be tentatively explained as follows: When a microorganism is viable, the cell membrane acts to retard penetration of the dye into the cell, thus restricting contact between the dye and the D.N.A., resulting in diminished uptake of dye. When the microorganism is non-viable, the cell membrane is in a ruptured condition and therefore presents no barrier to penetration by the dye, resulting in enhanced uptake of dye. The effect is that, because of differential absorption, stained viable and non-viable microorganisms fluoresce at different wavelengths: for example, using acridine orange dye, the viable microorganisms fluoresce green of wavelength 540 nm and non-viable microorganisms fluoresce orange-red of wavelength 665 nm.

When a dry preparation of microorganisms is used, it is possibly steric effects in the D.N.A. molecule which enable viable/non-viable discrimination. The effect of fixing the phosphate treated microorganisms to a slide kills them but, in those which were viable prior to treatment with phosphate and fixing, the D.N.A. molecules retain the highly ordered double-helix structure whereas, in those which were non-viable, the helices are disorganised. Disorganisation of the D.N.A. structure results in a reduced number of available dye-receptor sites due, probably, to steric hindrance to absorption of the phosphate and dye. Thus viable microorganisms are characterised by a high degree of absorption with associated high fluorescence (e.g. yellow-orange, 630 nm with acriflavine) and non-viable by low fluorescence (e.g. green, 540 nm with acriflavine).

An advantage of this invention is that it makes possible the counting of not only viable microorganisms (as with the standard colony-count technique) but also non-viable microorganisms. The non-viable cell count is of importance in that it indicates the microbiological history of the sample. For example, if a manufacturer were to sterilise a spoiled foodstuff then a standard colony-count would show the absence of viable microorganisms. However, the present method would reveal that at some time the food had contained numbers of microorganisms.

To enumerate the microorganisms in the sample, the area of stained preparation may be visually scanned under the microscope from the top to the bottom and from side to side. Alternatively, the microorganisms may be enumerated by means of an image analysing system using a photomultiplier sensing device which provides a digital readout of units, such as microorganisms fluorescing at a given wavelength.

The invention will now be described by way of illustration in the following Examples.

EXAMPLE 1

1.
(a) an area of 10mm. square is etched on glass slides (76 × 25mm. × 0.8–1.0mm. thick).
(b) alternatively the etched area of application may be 40mm × 2.5mm 2. The slides are immersed overnight in a fresh 2% solution of "RBS 25 + " (Trade Mark) detergent. The slides are gently washed in the solution, and well rinsed in cold and then in hot water. The slides are dried in a warm oven on draining racks for 10 to 15 minutes.

3.
(a) Pieces of meat weighing 10 g were excised aseptically from a larger piece, innoculated with test organisms and then swirled for 2 minutes by hand in a total of 100 ml of Ringer's solution.
(b) 10 microlites of the resulting liquid were placed in the centre of the etched area and carefully spread, using a fine straight wire, to cover the etched area completely.
(c) The preparation was allowed to dry for 15 minutes at 20° C.
(d) The preparation was fixed with 96% ethyl alcohol for 10 min at 20° C.
(e) Alcohol was drained off and the slide allowed to dry for 10 minutes at 20° C.
(f) A solution of 0.01% acriflavine in M/15 phosphate buffer pH 7.2. was placed on the slide for 10 minutes at 20° C.
(g) The stained preparation was rinsed gently in running water for 15 seconds.
(h) The water was drained off and the slide allowed to dry for 10 minutes at 20° C.

4. The preparation was examined with a Leitz Orthoplan microscope using a special fluorite objective X40/0.85 for uncovered fluorescent smears, giving a total magnification of 500X. A high pressure mercury vapour lamp HB200 light source was used, with incident illumination via a Ploem unit using BG12 3 mm +

BG38 as excitation filters. The Ploem mirror number 3 was used together with barrier filter K530.

The staining procedure described above in paragraph 3 was carried out in a dimly lit room. (If the slide was not to be examined immediately or was required for further examination, it was stored in the dark). Sunlight or artificial light causes fading of the stained preparation.

The viable cells in the sample fluoresced as an orange colour while non-viable cells were green.

The cells were counted visually using a scanning technique as follows:

Depending on the number of bacteria present in the sample, the number of fields examined was generally between 16 and 40. The reasons for the selection of this range of fields will be explained in the discussion. The movement between fields was performed blind to ensure a random selection of fields.

The mean number of organisms per field may be calculated knowing the total number of bacteria counted and the number of fields viewed. This figure is multiplied by a factor of 982 to give the total number of bacteria in 10μl. The degree of precision of each calculation was determined by reference to tables of Schedules of Precision, Cassel.

Examples of results are reported in the Tables below which give, for comparison, the results obtained by a colony-count on the same sample:

Tables 1 to 4 show the results of colony-counts and microscope counts (orange-fluorescing cells) of meat samples inoculated with different test strains. Column A shows the mean colony-count per gram column B, the standard deviation of this value. Column C shows the calculated number of viable microorganisms by the technique of this invention and column D gives the 90% Confidence Interval of this value. Column E shows number of microorganisms counted and the number of fields viewed.

Replicates of plate counts obey a normal distribution. The distribution in the case of microscope technique is Poisson in nature but can be approximated by the normal distribution when more than 15 organisms are counted. The Confidence Interval (Column D) predicts with 90% probability the limits of the "true" values of micro-organisms per gram from the Observed value (Column C).

It can be seen that the higher the number of microorganisms counted the smaller the value of the 90% Confidence Interval and the greater the precision of the technique.

The reproducibility of the counting of stained preparations prepared according to the method described above is shown in Table 1 Expt. 1. Table 2 Expts. 1, 2, 3, Table 3 Expts. 1, 4 and Table 4 Expt. 1 where two or more preparations were counted for each sample.

Table 1

| E. coli | Colony count A mean/gram | B S.D. | Enumeration by the Method of invention C number/gram | D 90% Confidence interval | E Number of bacteria and fields counted |
|---|---|---|---|---|---|
| Expt. 1 | $11.4 \times 10^6$ | ± 0.7 | $11.2 \times 10^6$ | ± 1.34 (± 12%) | 190 : 17 |
|  |  |  | $10.0 \times 10^6$ | ± 1.20 (± 12%) | 158 : 16 |
| 2 | $7.8 \times 10^6$ | ± 0.9 | $9.0 \times 10^6$ | ± 1.07 (± 12%) | 179 : 20 |
| 3 | $5.25 \times 10^6$ | ± 0.4 | $7.2 \times 10^6$ | ± 1.08 (± 15%) | 123 : 25 |
| 4 | $2.08 \times 10^6$ | ± 0.14 | $2.9 \times 10^6$ | ± 0.53 (± 18%) | 73 : 25 |
| 5 | $1.31 \times 10^6$ | ± 0.2 | $3.1 \times 10^6$ | ± 0.75 (± 24%) | 52 : 17 |
| 6 | $1.15 \times 10^6$ | ± 0.13 | $1.3 \times 10^6$ | ± 0.51 (± 39%) | 24 : 19 |
| Meat Control | $1.0 \times 10^2$ −$6.6 \times 10^2$ |  | less than $4 \times 10^3$ |  | 0 : 30 |

Table 2

| Ps. Fluo-rescens | Colony count A mean/gram | B S.D. | Enumeration of the Method of invention C Number/gram | D 90% confidence interval | E Number of bacteria and fields counted |
|---|---|---|---|---|---|
| Expt. 1 | $1.92 \times 10^6$ | ± 0.28 | $2.17 \times 10^6$ | ± 0.36 (± 15%) | 107 : 40 |
|  |  |  | $1.60 \times 10^6$ | ± 0.32 (± 20%) | 65 : 32 |
| 2 | $1.17 \times 10^6$ | ± 0.30 | $8.6 \times 10^5$ | ± 2.3 (± 27%) | 38 : 48 |
|  |  |  | $9.7 \times 10^5$ | ± 3.1 (± 32%) | 24 : 27 |
| 3 | $3.2 \times 10^5$ | ± 0.18 | $4.5 \times 10^5$ | ± 1.24 (± 27%) | 31 : 39 |
| Meat Control | $1.5 \times 10^3$ |  | $4.25 \times 10^5$ less than $4 \times 10^3$ | ± 1.51 (± 31%) | 26 : 34 |

Table 3

| Staph. aureus | Colony count A mean/gram | B S.D. | Enumeration by the Method of invention C number/gram | D 90% Confidence interval | E Number of bacteria and fields counted |
|---|---|---|---|---|---|
| Expt. 1 | $1.32 \times 10^6$ | ± 0.27 | $1.95 \times 10^6$ | ± 0.30 (± 18%) | 78 : 24 |
|  |  |  | $1.92 \times 10^6$ | ± 0.38 (± 22%) | 54 : 17 |
|  |  |  | $1.66 \times 10^6$ | ± 0.39 (± 28%) | 37 : 30 |
| 2 | $4.28 \times 10^5$ | ± 0.65 | $5.85 \times 10^5$ | ± 2.28 (± 45%) | 15 : 29 |
| 3 | $1.62 \times 10^5$ | ± 0.39 | $1.32 \times 10^5$ | − ( 50%) | 8 : 36 |
| 4 | $3.47 \times 10^4$ | ± 0.73 | $2.64 \times 10^4$ | − ( 50% | 4 : 23 |
|  |  |  | $2.00 \times 10^4$ | − ( 50%) | 3 : 23 |
| Meat Control | $6.0 \times 10^2$ |  | less than $4 \times 10^3$ |  | 0 : 30 |

Table 4

| Bacillus sp. | Colony count A mean/gram | B S.D. | Enumeration by the Method of invention C number/gram | D 90% Confidence interval | E Number of bacteria and fields counted |
|---|---|---|---|---|---|
| Expt. 1 | $5.9 \times 10^4$ | ± 1.8 | $1.58 \times 10^5$ | — (50%) | 6 : 38 |
|  |  |  | $1.97 \times 10^5$ | — (50%) | 6 : 28 |
|  |  |  | $5.4 \times 10^4$ | — (50%) | 2 : 36 |
| 2 | $4.2 \times 10^4$ | ± 0.6 | $3.96 \times 10^4$ | — (50%) | 2 : 45 |
| Meat Control | $2 \times 10^3$ |  | less than $4 \times 10^3$ | 0 : 30 |  |

The colony-counted method appears to give a smaller variation, in terms of standard deviation, than microscopic enumeration. However, the standard deviation and 90% Confidence Interval are not comparable. It can be said that the accuracy of the plate count was artificially enhanced by the use of 5 replicates, a situation which does not occur in routine quality-control procedures.

Many samples displayed close correlation between mean colony-counts and microscopic enumeration by the technique of the invention, the latter always being within the corresponding values of the colony-counts ± standard deviation.

In general enumeration using the microscopic technique was higher than the corresponding colony-count. This could be due to:
(a) the microscopic method using slides stained by this invention will estimate microorganisms singly, whereas colonies may derive from a single microorganism or a group of bacteria.
(b) there is the likelihood that a certain proportion of viable cells will not grow in laboratory recovery media, but which may multiply in foodstuffs. This is particularly relevant to "stressed" bacteria and bacterial spores. The units are still viable and are counted.

Microscope counts of meat or vegetable washings do not pose great problems regarding background fluorescence and the physical masking of fluorescing microorganisms. However, other foods, such as milk or egg powder, gave such high background fluorescence that counts were difficult using standard technique. Short fixation times in alcohol with subsequent treatment in 2% acetic acid successfully removed such background fluorescence. Unfortunately, this process also caused many of the microorganisms to be removed from the slide. In further experiments immersion of the preparation in a Coplin jar of water for 1 minute after treatment with alcohol-acetic acid for 30 minutes indicated that, with modifications, the microscopic technique was applicable to milk and egg based foods.

Using the staining technique of the invention, it was found that old cultures, particularly Gram negative rods, showed bright orange fluorescence together with dull green fluorescent cells. Cultures of Gram negative bacteria, sterilised by boiling at 100° C for 30 minutes, fluoresced uniformly dull green. This change from orange to green fluorescence was shown to be related to viability of the test culture. While old cultures of *Staphylococcus aureus* displayed both orange and green fluorescent cells, the heat treatment of a young culture by boiling for 30 minutes with subsequent staining showed all organisms to be orange fluorescent. However, pretreatment of the preparation with buffer solutions obviated such 'false-viable' reactions. The differences in reactions between Gram negative and Gram positive bacteria towards the fluorochromes illustrate important compositional differences between the two groups.

An advantage of the invention is the rapidity with which results can be obtained. The staining method of the Invention takes less than 1 hour for the actual staining procedure while the conventional colony-count requires several days incubation. Also the possibility exists of using a rapid optical scanning instrument to enumerate or detect the fluorescent cells. By adjusting the wavelength sensitivity of such an instrument, it will be possible to determine separately viable and non-viable cells.

The invention will now be further described by the following Examples which describe only the staining steps and the results obtained without discussing the counting technique.

EXAMPLE 2

Wet Preparation: Acridine Orange Stain

Procedure
1. A milk sample containing microorganisms is premixed with 0.62M phosphate buffer pH 7.2 to a given dilution.
2. One ml. of sample is pipetted into a container to which is added 1 ml of 0.01% solution of acridine orange in 0.62M phosphate buffer pH 7.2.
3. After agitation for 2 minutes at 25° C 0.02 ml of the sample mixture is pipetted on to a cleaned and dried carrier plate.
4. The applied sample is then covered with a clean, dry cover glass.
5. The microorganisms in preparation are then counted by incident illumination through a X' objective using a 450 n.m. excitation filter, a Ploem 3 dichroic mirror and a 530 n.m. barrier filter.

Comments

This staining procedure, which is also applicable to food and urine samples, results in viable microorganisms being predominantly green (540 nm) while nonviable microorganisms predominantly stained orange-red (665 nm).

The adjustment of the pH of the acridine orange solution to 7.2 from the normal pH of 4.5 enhanced the uptake of the fluorochrome by the nuclear material of the microorganisms, and the use of phosphate ions in the diluting buffer assisted the uptake of the fluorochrome and improved the level of emission of the fluorescing microorganism.

This technique is suitable for materials containing low levels of contaminating proteins, fats and other background material.

The mechanism of staining by acridine orange in this wet preparation is primarily due to binding with the nucleic acid. In viable microorganisms the cell membrane regulates the intake of fluorochrome, and the highly ordered state of the nucleic acids and proteins allows for minimal binding of the fluorochrome, resulting in emission of green fluorescene at around 540 nm. The non-viable microorganisms lose the selective permeability of the cell membrane, permitting fluorochrome to bind in great quantities, giving orange-red fluorescence at 665 nm.

EXAMPLE 3

Wet Preparation: Total Count in Urine

Procedure
1. Urine samples are diluted with 1:1 volumes of 0.5M phosphoric acid and 0.2 M oxalic acid pH 2.0 to effect acid hydrolysis.
2. Add 0.2 ml of 0.01% ethidium bromide and hold at 40° C for 10 minutes.
3. The sample is adjusted to pH 6.5 using 0.5M disodium hydrogen phosphate in solution.
4. Proceed as in Example 2 steps at pH 7.2

Comments

This procedure was designed to disorganise the nucleic acid and tertiary structure of proteins in the microbial cell by acid hydrolysis, resulting in the formation of acidic and aldehydic groups. These groups in the presence of phosphate groups at pH 6.5 bind large numbers of ethidium bromide molecules resulting in all microorganisms showing orange-red fluorescence.

EXAMPLE 4

Wet Preparation: Pre-irradiation Yeast Stain

Procedure
1. One ml. of a sample containing yeasts in aqueous suspension is combined with 1 ml of a saturated aqueous solution of fluorescein diacetate in 0.62 M phosphate buffer at pH 6.8 and held at 25° for 30 seconds.
2. To the above suspension is added 2 ml. of 0.01% acridine orange in M/15 phosphate buffer at pH 7.2
3. Proceed as in Example 2 steps.
4. Irradiate the prepared sample at 450 nm for 5 seconds.
5. Illuminate the prepared sample at 360 nm and count yeast cells using the Ploem 1 dichroic mirror and a 430 nm barrier filter.

Comments

The reason for the enhancement of the levels of emission of yeast cells by pre-irradiation at 450 nm is not clear. It is considered that the preliminary treatment of yeast cells with fluorescein diacetate provides an initial link with active sites; the effect of acridine orange in the presence of phosphate ions being to link with the fluorescein diacetate. Pre-irradiation at 450 nm may photocatalyse a reaction between the fluorochrome groups, reducing the quantity of excitational energy converted into thermal energy, producing a higher quantum yield of fluorescence at the longer wavelength.

EXAMPLE 5

Wet Preparation: Total Staining of Bacteria in Milk or Urine Samples

Procedure
1. 1 ml of milk is mixed with 1 ml of 0.025% aqueous acridine yellow in 0.62M phosphate buffer at pH 5.6 and held for 30 seconds at 25°.
2. Two ml. of a mixture of 2% orthophosphoric acid and 8% tartaric acid is added to the preparation to give a pH of 1.5 and hold at 40° C for 10 minutes.
3. Adjust pH 6.5 using 0.5M sodium dihydrogen phosphate solution.
4. 0.02 ml of the sample is pipetted on to a cleaned and dried carrier plate.
5. Proceed as for Example 2, steps 4 and 5.

Comments

All bacteria fluoresce a uniform bright yellow (575 nm) against a dark background with no staining of the fat globules or milk-protein.

Acridine yellow has a similar affinity for microbial DNA as acridine orange but gives much less non-specific background fluorescence in this wet preparation.

EXAMPLE 6

Wet Preparation: Total Bacteria in Milk or Urine Sample

Procedure
1. One ml of milk sample is diluted to 1:10 with water.
2. Prepare a 1.0% solution of Sudan Black B in cellosolve and dilute to 0.1% in water containing 0.25% sodium hexametaphosphate pH 6.5. With agitation add 1 ml of this system to the milk sample and hold for 1 minute at 25°.
3. With agitation add 1 ml 0.15% tetra methyl-oxamethinecyanine ester in water and hold for 1 minute at 25°.
4. 0.02 ml of the sample is then pipetted on to a cleaned and dried carrier plate.
5. Proceed as in Example 2 steps 4 and 5 using excitation at 360 nm, the Ploem 1 dichroic mirror and the 430 nm barrier filter.

Comments

Treatment of the milk sample with Sudan Black B eliminates background staining by fat globules and the agitation during addition of the reagents ensures the submicroscopic precipitation of the casein fraction. Bacteria stain an intense blue colour (480 nm) against a black background.

EXAMPLE 7

Wet Preparation: Total Count in Milk Samples

Procedure
1. To 1 ml of a 1:10 dilution of milk in water add 1 ml of 1% aqueous solution of chloroxylenol pH 8.5. Allow to act for 30 seconds at 25° with agitation. Chloroxylenol is a defatting agent.
2. Add 1 ml of 0.5% malachite green (a background stain) in water pH 3.5 and allow to act for 30 seconds at 35° with agitation.
3. Add 1 ml of 0.01% acridine orange in M/15 phosphate buffer pH 7.2. Allow to act for 2 minutes at 25°.
4. 0.02 ml of the sample is then pipetted onto a cleaned and dried carrier plate.
5. Proceed as in Example 2 steps 4 and 5 employing excitation at 450 nm, the Ploem 3 dichroic mirror and the 530 nm barrier filter.

Comments

In this procedure the ability of malachite green to react with milk fat and casein was utilised to block access to the fluorochrome.

Using a pretreatment with chloroxylenol, the permeability of the bacteria towards acridine orange was enhanced.

Using this system bacteria fluoresced a bright green-yellow 565 nm against a blue-green background 520 nm. There was little evidence of fat globules or casein in these preparations.

EXAMPLE 8

Wet Preparation: Total Count in Urine (High Contrast Stain)

Procedure
1. 1 ml urine is mixed with approximately 1 ml 0.75M orthophosphoric acid to pH 2.0.
2. Add 0.5 ml of 0.1% aqueous sodium thiosulphate and 0.2 ml of 0.01% aqueous ethidum bromide and hold the mixture at 40° for 10 minutes.
3. Add 0.5 ml of 0.05% aqueous sodium hypochlorite and adjust the pH to 6.5 using 0.5M disodium hydrogen phosphate solution.
4. Prepare and examine as in Example 7, steps 4 and 5.

EXAMPLE 9

Dry Preparation: Acriflavine Stain

Procedure
1. A milk sample containing micro-organisms is premixed with 0.62 phosphate buffer pH 7.2 to a known dilution.
2. A 0.01 ml aliquot of the sample is applied to a clean dry carrier plate and spread on 1 sq. cm. using a sterile applicator.
3. The applied sample is dried at 25° C.
4. The applied sample is fixed to the carrier plate by covering with 95% (w/v) ethanol for 10 minutes at 25° C.
Alternative fixative solutions also used include
   (a) 1:1 vols. 95% ethanol:20% acetic acid
   (b) 10% formalin.
5. The fixed preparation is now drained and rinsed with 0.62 phosphate buffer to pH 7.2.
6. The preparation is then covered with 0.01% acriflavine in 0.62 phosphate buffer at pH 7.2 for 10 minutes at 25° C.
7. The preparation is then washed with water and allowed to dry in air at 25° C.
8. The preparation is then counted by incident illumination, without a cover glass, through a X40 objective with an excitation of 450 nm a Ploem 3 dichroic mirror and a 530 nm barrier filter.

Comments

This staining procedure which is also applicable to food and urine samples, results in viable microorganisms being predominantly stained yellow-orange while non-viable microorganisms predominantly stain green.

Under the conditions of staining of microorganisms by this dry preparation, it is considered that the binding of the fluorochrome acriflavine occurs at the cell wall with layers of fluorochrome being built up. In viable cells this results in a high concentration of acriflavine units resulting in the yellow-orange emission wavelength of 630 nm. In non-viable cells the disorganization of the binding sites on the cell wall results in the absorption of acriflavine only at low levels, thus providing a green fluorescence at 540 nm.

EXAMPLE 10

Dry Preparation: Viable-Non-viable Differentiation of Gram Negative Bacteria

Procedure
1-5 Sample prepared as in Example 7 steps 1-5.
6. The preparation is then immersed in a bath containing 1N hydrochloric acid at 60° C for 5 minutes to effect acid hydrolysis.
7. The preparation is then removed and washed in water.
8. The preparation is then immersed in a solution containing 1 ml of 5% acriflavine and 10% potassium metabisulphate in 0.1N hydrochloric acid diluted with 5% potassium metabisulphite in 0.1N hydrochloric acid for 10 minutes at 25° C.
9. The preparation is then removed, washed with water and dried in air at 25° C.
10. The preparation is then examined as in Example 9, step 8.

Comments

This staining procedure results in the better differentiation of viable (orange-fluorescent) from non-viable (green-fluorescent) Gram negative micro-organisms.

The acid hydrolysis treatment (step 6) releases available aldehydric groups in the D.N.A. molecule, forming, in effect a polyaldehyde. In the viable microorganisms the D.N.A. is highly ordered and the resultant polyaldehyde is also highly ordered. The sulphur dioxide applied in step 8 combines with the aldehyde groups and allows the fluorochrome to form an equally spaced matrix, and the associated complex results in a massive uptake of acriflavine with resultant yellow-orange fluorescence.

In the non-viable Gram negative microorganism the D.N.A. is denatured and it and the resultant polyaldehyde are highly unordered, resulting in poor association of the acriflavine, low uptake and therefore the emission of green fluorescence. By the application of heat to the sample for 10 minutes at 115° prior to step 6, differentiation between Gram positive and Gram negative bacteria may be obtained. Following this procedure Gram positive bacteria fluoresce orange and Gram negative bacteria fluoresce green.

EXAMPLE 11

Dry Preparation: Viable-Non-viable Differentiation of Gram Positive Bacteria

Procedure
1. Samples containing cultures of Gram positive microorganisms e.g. *Staphylococcus aureus* were diluted 1:1 with 0.1M sodium barbitone-hydrochloric acid buffer at pH 5 containing 100 p.p.m. calcium. Each suspension was heated for 10 minutes at 121° C and then cooled rapidly to 4° C.
2. Proceed as for Example 9, steps 2 to 5.
3. Proceed as for Example 10, steps 6 to 10.

Comments

The staining of Gram positive bacteria by acriflavine differs from that shown by Gram negative bacteria. *Staph. aureus* differs from Gram negative bacteria in that it contains teichoic acid, a ribitol phosphate polymer, in the cell wall and also contains greater quantities of polysaccharides than do Gram-negative bacteria.

In *Staph. aureus* it is considered that acriflavine combines strongly with teichoic acid, through phosphate ester links, and/or with the polysaccharide fraction also through phosphate or ester links.

The replacement of phosphate buffer by barbitone buffer reduces the stability of these ester links, and the calcium included in the heating system blocks other phosphate groups.

Thus, following step 1 *Staph. aureus* demonstrates a non-viable, i.e., green fluorescent staining reaction compared with a viable staining reaction in its absence.

EXAMPLE 12

Dry Preparation: Gram Positive Bacteria in Milk

Procedure
1. A 1:10 dilution of milk in water is prepared and fixed with alcohol as described in Example 9 steps 1-5.
2. The fixed preparation is immersed in 1.0% aqueous 4,4'-diamino 2,2'-stilbenedisulphonic acid ester for 5 minutes at 25° C.
3. The preparation is then rinsed in water at 25° C.
4. The preparation is then immersed in 0.01% acridine orange in 0.62 phosphate buffer at pH 7.2 for 5 minutes at 25° C.
5. The preparation is then examined as Example 2 step 5.

Comments

Using this procedure Gram positive bacteria were found to show orange fluoroscence while Gram negative bacteria were a dull brown colour. The general background was green/blue with low interference by casein and the milk fat globule membrane. The uptake of acridine orange by casein and the fat globules was blocked by step 2.

I claim:

1. A method of staining viable microorganisms or a mixture of viable and of non-viable microorganisms comprising reacting said microorganisms, suspended in a liquid medium, with phosphate ions, whereby phosphate ions react at active sites on the microorganisms to produce phosphate derivatives of the microorganisms having, at said sites, polydentate phosphate groups, reacting the phosphate derivatives with a phosphate-reactive fluorochrome dye, which thereby combines chemically with the microorganisms via the intermediate phosphate groups, and examining the thus-fluorochrome-dyed microorganisms with fluorescence-activating ultraviolet light for the presence, relative amounts or numbers of viable and non-viable microorganisms suspended in the liquid medium.

2. A method according to claim 1 which comprises reacting the fluorochrome dye with the phosphate derivatives of the microorganisms while such derivatives are supsended in the liquid medium and microscopically examining resulting fluorochrome-dyed microorganisms while the latter are still in a liquid medium.

3. A method according to claim 1 which comprises applying the phosphate derivatives to a carrier, fixing the derivatives on the carrier with a liquid solvent to obtain a fixed sample, contacting the fixed sample with the fluorochrome dye to obtain a stained sample, drying the stained sample to produce a dry specimen for microscopic examination in the dry state.

4. A method according to claim 1 which comprises increasing the number of active sites on the microorganisms by chemical modification before reacting the microorganisms with phosphate ions, the chemical modification being effected by a chemical treatment selected from the group consisting of methylation, esterification, hydrolysis, oxidation and reaction with sulphur dioxide.

5. A method according to claim 1 wherein the fluorochrome dye is a member selected from the group consisting of lissamine-rhodamine B, acridine orange, primuline, ethidium bromide, acriflavine, tetramethyloxamethine-cyanine ester, eosin Y, auramine, rhodamine B, rhodamine 3G, fluorescein, fluorescein diacetate and thionine.

6. A method according to claim 1 which further comprises treating the phosphate derivatives with an optical-brightening agent.

7. A method according to claim 6 wherein the optical-brightening agent is 4,4'-diamino-2,2'-stilbenedisulphonic acid ester.

8. A method of enumerating viable microorganisms or enumerating and/or discriminating between viable and non-viable microorganisms in a specimen containing both types of microorganisms, comprising reacting phosphate ions with the microorganisms while the latter are suspended in a liquid medium, whereby phosphate ions react at active sites on the microorganisms to produce phosphate derivatives of the microorganisms, having, at said sites, polydentate phosphate groups, reacting the suspended phosphate derivatives with a solution of fluorochrome dye to stain said derivatives, and counting the number of or discriminating between the stained microorganisms in said stained suspension in a thin layer under a microscope with illumination of the stained suspension with fluorescence-activating ultraviolet light.

9. A method according to claim 8 which comprises adding the phosphate ions and the fluorochrome dye in a single solution containing both to a suspension of the microorganisms in a liquid medium.

10. A method of enumerating viable microorganisms or enumerating and/or discriminating between viable and non-viable microorganisms in a specimen containing both types of microorganisms, comprising reacting phosphate ions in solution with the microorganisms while the latter are suspended in a liquid medium, whereby phosphate ions react at active sites on the microorganisms to produce phosphate derivatives of the microorganisms having, at said sites, polydentate phosphate groups, applying a measured sample of said derivatives to a carrier, drying the sample, fixing the resulting dry sample to the carrier with a liquid solvent to obtain a sample fixed on the carrier, immersing the fixed sample in a solution of fluorochrome dye to stain said sample, drying the resulting stained sample and counting and/or discriminating between the stained microorganisms by examination under a microscope with illumination of the sample with fluorescence-activating ultra-violet light.

* * * * *